(12) United States Patent
Yoshida et al.

(10) Patent No.: US 8,147,807 B2
(45) Date of Patent: Apr. 3, 2012

(54) ORAL COMPOSITION FOR DENTAL PURPOSES

(75) Inventors: Yasuhiro Yoshida, Okayama (JP); Naoko Namba, Okayama (JP); Noriyuki Nagaoka, Okayama (JP); Kaori Yoshimoto, Okayama (JP); Shogo Takashiba, Okayama (JP); Kazuomi Suzuki, Okayama (JP); Hiroshige Ishino, Kurashiki (JP); Takahiro Sekiguchi, Kurashiki (JP); Koichi Okada, Kurashiki (JP)

(73) Assignees: National University Corporation Okayama University, Okayama-shi (JP); Kuraray Medical Inc., Kurashiki-shi (JP)

( * ) Notice: Subject to any disclaimer, the term of this patent is extended or adjusted under 35 U.S.C. 154(b) by 494 days.

(21) Appl. No.: 12/374,215

(22) PCT Filed: Jul. 18, 2007

(86) PCT No.: PCT/JP2007/064185
§ 371 (c)(1),
(2), (4) Date: Feb. 9, 2009

(87) PCT Pub. No.: WO2008/010517
PCT Pub. Date: Jan. 24, 2008

(65) Prior Publication Data
US 2010/0240714 A1    Sep. 23, 2010

(30) Foreign Application Priority Data
Jul. 20, 2006  (JP) .................................. 2006-198367

(51) Int. Cl.
*A61K 8/00* (2006.01)

(52) U.S. Cl. ................ 424/49; 424/53; 424/57
(58) Field of Classification Search .............. 424/49–58; 514/358
See application file for complete search history.

(56) References Cited

U.S. PATENT DOCUMENTS

| 3,147,182 A * | 9/1964 | Grutter et al. ................ 424/401 |
| 3,956,480 A | 5/1976 | Dichter et al. |
| 4,948,784 A | 8/1990 | Mori et al. |
| 5,100,877 A | 3/1992 | Mori et al. |
| 5,202,111 A * | 4/1993 | Spaltro et al. .................. 424/49 |
| 5,578,598 A | 11/1996 | Abe et al. |
| 5,658,915 A | 8/1997 | Abe et al. |
| 2004/0105823 A1 | 6/2004 | Kamasaka et al. |
| 2006/0222603 A1 | 10/2006 | Kamasaka et al. |
| 2008/0038210 A1 | 2/2008 | Yano et al. |
| 2010/0330005 A1 | 12/2010 | Yoshida et al. |

FOREIGN PATENT DOCUMENTS

| JP | 7 17839 | 1/1995 |
| JP | 9 175965 | 7/1997 |
| JP | 9 286712 | 11/1997 |
| JP | 2000 154127 | 6/2000 |
| JP | 2002 29948 | 1/2002 |
| JP | 2002 325556 | 11/2002 |
| JP | 2002 325557 | 11/2002 |
| JP | 2005 29484 | 2/2005 |
| JP | 2005 47855 | 2/2005 |
| JP | 2005 330269 | 12/2005 |
| JP | 2005 330270 | 12/2005 |
| JP | 2006 117574 | 5/2006 |
| WO | 87 07142 | 12/1987 |
| WO | 92 09198 | 6/1992 |

OTHER PUBLICATIONS

Tarelli, E. et al., "Direct Preparation Of Cyclodextrin Monophosphates", Carbohydrate Research 302, pp. 27-34 (1997).

* cited by examiner

*Primary Examiner* — Patricia A Duffy
*Assistant Examiner* — Dennis J Parad
(74) *Attorney, Agent, or Firm* — Oblon, Spivak, McClelland, Maier & Neustadt, L.L.P.

(57) ABSTRACT

A dental composition for oral use, containing a phosphorylated saccharide (a), a cationic bactericidal agent (b) and a solvent (c). By using the dental composition for oral use of the present invention, the adhesion of the bacteria in the oral cavity to the surfaces of the teeth can be suppressed for a long period of time; therefore, the dental composition for oral use can be suitably used for, for example, a mouse-wash agent, a dentifrice agent, a gargling agent, a mouse spray, a coating agent or a bonding agent to tooth surface or a dental prosthetic, a hypersensitive inhibitor, a therapeutic agent for periodontal diseases, that is applied to a periodontal pocket, or the like.

8 Claims, 3 Drawing Sheets

ORAL COMPOSITION FOR DENTAL PURPOSES

This application is a 371 of PCT/JP07/64185 filed Jul. 18, 2007.

TECHNICAL FIELD

The present invention relates to a dental composition for oral use. More specifically, the present invention relates to a dental composition for oral use for oral use capable of suppressing bacterial adhesion to teeth and mucosal membrane surface in the oral cavity, whereby consequently being capable of suppressing the formation of dental plaques and dental calculi on the surface of the teeth, and further being useful as prophylactic materials for dental caries, periodontal diseases, and halitosis.

BACKGROUND ART

Diseases in the oral cavity include dental caries, periodontal diseases, such as gingivitis and periodontitis, stomatitis, and the like. Among them, the dental caries is a representative disease of teeth, which is developed due to the dissolution of teeth by an acid produced by microorganisms in the oral cavity. Among the microorganisms in the oral cavity, *Streptococcus mutans*, which may be hereinafter simply referred to as *S. mutans*, is considered as one of the pathogenic bacteria for dental caries. In addition, the periodontitis which is an inflammatory disease of a periodontal tissue is considered to be developed due to the bacteria in the oral cavity. In general, if the bacteria causing dental caries as described above are adhered to the surfaces of the teeth, the dental plaques are formed, which are considered to be causative of various diseases in the oral cavity, such as dental caries and periodontal diseases.

For this reason, a dental composition for oral use which applies the technique of coating surfaces of the teeth with a specified drug or a polymer, thereby suppressing the adhesion of bacteria, to inhibit the formation of plaques has been proposed. Among them, a composition containing a cationic bactericidal agent, such as cetyl pyridinium chloride, benzethonium chloride, or chlorhexidine, the composition having a high bactericidal activity against bacteria in the oral cavity has been well used for this purpose. However, the cationic bactericidal agent as described cannot be sustained on the surfaces of the teeth for a long time when used alone, so that the agent has disadvantages such as lowered sustainability of the effects, thereby making it poor in actual use.

In order to solve the problems as mentioned above, for example, a technique of accelerating an adsorption action of a bactericidal agent by using a lower alkyl ester of an N-long-chained acyl basic amino acids in combination with a cationic bactericidal agent (see, for example, Patent Publication 1), a technique of using a polyphosphoric acid and a polyglycerol fatty acid ester in combination with a cationic bactericidal agent (see, for example, Patent Publication 2), and a technique of using a polymer of ammonium dimethyldiallyl chloride as a cationic bactericidal agent (see, for example, Patent Publication 3) have been disclosed.

Patent Publication 1: Japanese Patent Laid-Open No. Hei 9-286712
Patent Publication 2: Japanese Patent Laid-Open No. 2006-117574
Patent Publication 3: Japanese Patent Laid-Open No. Hei 9-175965

SUMMARY OF THE INVENTION

The present invention relates to a dental composition for oral use, containing a phosphorylated saccharide (a), a cationic bactericidal agent (b) and a solvent (c).

DETAILED DESCRIPTION OF THE INVENTION

In order to exhibit an effect of suppressing bacterial adhesion even in according to the conventional techniques, since the compositional ratio of the bactericidal agent in the composition must be made into a relatively high concentration, a disadvantage in safety of live body is likely to be caused, and the residual property of the bactericidal agent on the surfaces of the teeth is not yet sufficient, thereby giving rise to a disadvantage that it is difficult to allow the effect to last. Therefore, the development of a dental composition for oral use so as to be capable of effectively inhibiting the adhesion of bacteria in the oral cavity to the surfaces of the teeth by a convenient method, and allowing the effect to last for a long time period has been desired.

The present invention has been accomplished in view of meeting the above needs, and the present invention relates to a dental composition for oral use which is capable of suppressing the adhesion of the bacteria in the oral cavity to surfaces of the teeth for a long time period by enhancing the residual property of a cationic bactericidal agent to the surfaces. Also, the present invention relates to a dental composition for oral use having excellent safety of live body that is capable of effectively suppressing the bacterial adhesion with a bactericidal agent in an even smaller formulation amount.

The present inventors have found that a phosphorylated saccharide serves to accelerate the adsorption of a cationic bactericidal agent to surfaces of the teeth and enhance the residual property on the surfaces. The present invention has been perfected thereby.

If a dental composition for oral use of the present invention is used, the adhesion of bacteria in the oral cavity to surfaces of the teeth can be suppressed for a long period of time, so that the plaques and the dental calculi are less likely to be adhered to the surfaces of the teeth, thereby contributing to the prevention of dental caries, periodontal diseases, halitosis, deglutition pneumonia, or the like. Also, when the composition is applied to a periodontal pocket, plaques are less likely to be formed in a gap between the teeth and the gingivae, thereby contributing to the prevention and the treatment of periodontal diseases. In addition, since the composition of the present invention exhibits a high effect even with a smaller amount of a bactericidal agent formulated in the composition, the composition also has excellent safety upon the use of the composition of the present invention in the oral cavity.

The present invention will be described more specifically hereinbelow.

The dental composition for oral use of the present invention contains a phosphorylated saccharide (a), a cationic bactericidal agent (b) and a solvent (c).

The phosphorylated saccharide (a) in the present invention is used for the purposes of accelerating the adsorption of a cationic bactericidal agent (b) to surfaces of the teeth and enhancing the residual property on the surfaces. Although the reasons why the adsorption and the residual property of the bactericidal agent in the surfaces of the teeth are especially remarkably improved by using the phosphorylated saccharide (a) and the cationic bactericidal agent (b) together are not clear, the present inventors assume to be as follows. Specifically, a phosphorylated saccharide has a phosphate group in the molecule, the phosphate group having a high affinity to hydroxyapatite, a main component of the teeth, so that the phosphorylated saccharide is more likely to be adsorbed to and held on the surfaces of the teeth. In the present invention, since a cationic bactericidal agent is electrostatically or physically held via the phosphorylated saccharide, it is assumed that the cationic bactericidal agent can be detained specifically to the surfaces of the teeth, and the action lasts. The phrase "cationic bactericidal agent is electrostatically held" as used herein refers to a state where a cationic bactericidal agent is adsorbed to surfaces of the teeth in the form of a complex by electrostatically forming a complex of mainly an anionic phosphorylated saccharide and a cationic bactericidal agent, and the phrase "cationic bactericidal agent is physically held" refers to a state where a cationic bactericidal agent is held by intertwining with a chained phosphorylated saccharide.

The phosphorylated saccharide (a) includes, for example, those obtained by subjecting a part or all of hydroxyl groups of monosaccharides, polysaccharides, and sugar alcohols to phosphorylation. In the phosphorylated saccharide (a), a part or all of the phosphorylated saccharide may be in the form of salts. These salts are exemplified by sodium salts, potassium salts, calcium salts, magnesium salts, ammonium salts, and the like.

The monosaccharide includes, for example, glucose, galactose, fructose, mannose, xylose, arabinose, ribose, and the like. The polysaccharide includes, for example, agarose, pullulan, and the like. The sugar alcohols includes, for example, glycerol, erythritol, pentaerythritol, dipentaerythritol, arabitol, ribitol, xylitol, sorbitol, mannitol, galactitol, inositol, quercitol, and the like. Among them, pullulan is more preferably used from the viewpoint of being less likely to be metabolized by amylase or the like in the oral cavity, thereby less likely to serve as a nutrient for bacteria.

The phosphorylated saccharide usable in the present invention can be produced according to a known method by subjecting a hydroxyl group of at least one saccharide selected from the group consisting of the monosaccharides, the polysaccharides, and the sugar alcohols as mentioned above to phosphorylation. For example, a method of reacting with sodium metaphosphate described in *Carbohydrate Research* 302 (1997), 27-34, a method of reacting with sodium phosphate described in Japanese Patent Laid-Open Nos. 2005-330269 and 2005-330270, and the like are used. Furthermore, as described in WO 87/07142, a method of reacting phosphorus pentoxide and pullulan to give phosphorylated pullulan is preferably used.

As the phosphorylated saccharide usable in the present invention, those obtained by subjecting a hydroxyl group of at least one saccharide selected from the monosaccharides, the polysaccharides, and the sugar alcohols as mentioned above to phosphorylation can be used. The phosphorylated saccharide includes, for example, phosphorylated glucose, phosphorylated galactose, phosphorylated fructose, phosphorylated mannose, phosphorylated xylose, phosphorylated arabinose, phosphorylated ribose, phosphorylated agarose, phosphorylated pullulan, phosphorylated glycerol, phosphorylated erythritol, phosphorylated pentaerythritol, phosphorylated dipentaerythritol, phosphorylated arabitol, phosphorylated ribitol, phosphorylated xylitol, phosphorylated sorbitol, phosphorylated mannitol, phosphorylated galactitol, phosphorylated inositol, phosphorylated quercitol, and the like.

Among these phosphorylated saccharides, the phosphorylated pullulan is preferred, from the viewpoint of the effect of suppressing adhesion of bacteria by holding a cationic bactericidal agent, the production cost, and storage stability, and the like. Also, the phosphorylated pullulan is preferred from the viewpoint of being less likely to be metabolized with amylase or the like in the oral cavity, thereby making it less likely to serve as a nutrient for bacteria. In these phosphorylated saccharides, a phosphorylated saccharide obtained by subjecting a hydroxyl group derived from a saccharide to phosphorylation in an amount of 0.5 to 15% by number is preferred. Here, the number ratio of the hydroxyl groups that are phosphorylated in the phosphorylated saccharide can be calculated by measuring an amount phosphorus contained by performing elemental analysis of the phosphorylated saccharide, and obtaining the ratio assuming that the all of the measured phosphorus are derived from the hydroxyl groups that are subjected to phosphorylation (see Examples set forth below).

It is desired that the phosphorylated pullulan preferably usable in the present invention is those of which hydroxyl groups are subjected to phosphorylation in an amount of preferably from 0.5 to 15% by number, and more preferably from 2 to 10% by number. In addition, the phosphorylated pullulan has a preferred number-average molecular weight Mn within the range of from 5,000 to 500,000, and more preferably within the range of from 10,000 to 100,000, from the viewpoint of physically holding the cationic bactericidal agent.

The cationic bactericidal agent (b) usable in the present invention is a compound having a bactericidal action against the bacteria in the oral cavity, and the cationic bactericidal agent includes, for example, a quaternary ammonium salt represented by the following general formula (I):

[Ka 1]

(I)

wherein each of $R_1$, $R_2$, $R_3$, and $R_4$ is independently a substituted or unsubstituted, saturated or unsaturated, and branched or linear aliphatic group having 1 to 30 carbon atoms, for example, an alkyl group, an arylalkyl group, an alkoxyalkyl group, a polyoxyalkyl group, an alkylamide alkyl group, an alkylsulfamide alkyl group, a hydroxyalkyl group, a halogen atom-substituted alkyl group, or the like; or an aromatic group, for example, an aryl, an alkylaryl or the like, or two or three of any of $R_1$, $R_2$, $R_3$, and $R_4$ may be connected to form a ring; and $X^-$ is an anion selected from a halide (including, for example, a chloride, a bromide, or an iodide), an acetate, a citrate, a lactate, a glycolate, a phosphate, a nitrate, a sulfate, an alkyl sulfate, an aryl sulfate, an alkylaryl sulfate, a perchlorate, and a tetrafluoroborate.

Specific examples include dodecyltrimethylammonium chloride, tetradecyltrimethylammonium chloride, hexadecyltrimethylammonium chloride, octadecyltrimethylammonium chloride, dodecyldimethylbenzylammonium chloride, tetradecyldimethylbenzylammonium chloride, hexadecyldimethylbenzylammonium chloride, octadecyldimethylbenzylammonium chloride, octadecyldimethylbenzylammonium bromide, octadecyldimethylbenzylammonium iodide, (dodecylphenylmethyl)trimethylammonium chloride, dioctadecyldimethylammonium chloride, dioctadecyldibenzylammonium chloride, trioctadecylbenzylammonium chloride, octadecyltrihydroxyethylammonium chloride, and the like. In addition, the examples of the compounds of the general formula (I) include the following compounds.

[Ka 3]

(II)

wherein each of $R_5$, $R_6$, $R_7$, $R_8$, $R_9$, and $R_{10}$ is independently a substituted or unsubstituted, saturated or unsaturated, and branched or linear aliphatic group having 1 to 30 carbon atoms, for example, an alkyl group, an arylalkyl group, an alkoxyalkyl group, a polyoxyalkyl group, an alkylamide alkyl group, an alkylsulfamide alkyl group, a hydroxyalkyl group, a halogen atom-substituted alkyl group, or the like; or an aromatic group, for example, an aryl, an alkylaryl or the like, or two or three of any of $R_5$, $R_6$, $R_7$, $R_8$, $R_9$, and $R_{10}$ may be connected to form a ring;

$L_1$ is a substituted or unsubstituted divalent linking group, for example, an alkylene group, an arylene group, or an arylalkylene group; and $X^-$ is an anion selected from a halide (for example, a chloride, a bromide, or an iodide), an acetate, a citrate, a lactate, a

[Ka2]

In addition, the cationic bactericidal agent usable in the present invention includes a quaternary ammonium salt represented by the following general formula (II):

glycolate, a phosphate, a nitrate, a sulfate, an alkyl sulfate, an aryl sulfate, an alkylaryl sulfate, a perchlorate, and a tetrafluoroborate.

Specific examples of the compounds of the general formula (II) include a compound represented by the following general formula (III):

[Ka 4]

(III)

wherein n is an integer of from 2 to 12, and the following compounds, and the like.

[Ka 5]

In addition, the cationic bactericidal agent usable in the present invention includes a quaternary ammonium salt represented by the following general formula (IV):

[Ka 6]

(IV)

wherein $R_{11}$ is a substituted or unsubstituted, saturated or unsaturated, and branched or linear aliphatic group having 1 to 30 carbon atoms, for example, an alkyl group, an arylalkyl group, an alkoxyalkyl group, a polyoxyalkyl group, an alkyl amide alkyl group, an alkylsulfamide alkyl group, a hydroxyalkyl group, a halogen atom-substituted alkyl group, or the like; or an aromatic group, for example, an aryl, an alkylaryl, or the like; and $X^-$ is an anion selected from a halide (for example, a chloride, a bromide, or an iodide), an acetate, a citrate, a lactate, a glycolate, a phosphate, a nitrate, a sulfate, an alkyl sulfate, an aryl sulfate, an alkylaryl sulfate, a perchlorate, and a tetrafluoroborate.

Specific examples include dodecylpyridinium chloride, tetradecylpyridinium chloride, cetylpyridinium chloride, 12-methacryloyloxydodecylpyridinium bromide, and the like. Also, examples of the compounds of the general formula (IV) include the following compounds.

[Ka 7]

In addition, the cationic bactericidal agent usable in the present invention includes a pyridinium salt represented by the following general formula (V):

[Ka 8]

(V)

wherein $L_2$ is a substituted or unsubstituted divalent linking group, for example, an alkylene group, an arylene group, or an arylalkylene group; and $X^-$ is an anion selected from a halide (for example, a chloride, a bromide, or an iodide), an acetate, a citrate, a lactate, a glycolate, a phosphate, a nitrate, a sulfate, an alkyl sulfate, an aryl sulfate, an alkylaryl sulfate, a perchlorate, and a tetrafluoroborate.

Specific examples of the compounds of the general formula (V) include a compound represented by the following general formula (VI):

[Ka 9]

(VI)

wherein n is an integer of from 2 to 12.

In addition, the cationic bactericidal agent usable in the present invention includes a quaternary ammonium salt represented by the following general formula (VII):

[Ka 10]

(VII)

wherein each of $R_{12}$ and $R_{13}$ is independently a substituted or unsubstituted, saturated or unsaturated, and branched or linear aliphatic group having 1 to 30 carbon atoms, for example, an alkyl group, an arylalkyl group, an alkoxyalkyl group, a polyoxyalkyl group, an alkylamide alkyl group, an alkylsulfamide alkyl group, a hydroxyalkyl group, a halogen atom-substituted alkyl group, or the like; or an aromatic group, for example, an aryl, an alkylaryl or the like; and $X^-$ is an anion selected from a halide (for example, a chloride, a bromide, or an iodide), an acetate, a citrate, a lactate, a glycolate, a phosphate, a nitrate, a sulfate, an alkyl sulfate, an aryl sulfate, an alkylaryl sulfate, a perchlorate, and a tetrafluoroborate.

Specific examples of the compounds of the general formula (VII) include the following compound.

[Ka 11]

Among these cationic bactericidal agents, those compounds in which each of $R_1$ to $R_{13}$, which is a substituent on a nitrogen atom in any of the above general formulas, is independently a substituted or unsubstituted, saturated or unsaturated, and branched or linear alkyl group or arylalkyl group are preferred, and those in which the substituent is an unsubstituted, saturated or unsaturated, and branched or linear alkyl group or arylalkyl group are more preferred, and those in which the substituent is an unsubstituted, linear alkyl group or arylalkyl group are even more preferred.

In addition, among these cationic bactericidal agents, when consideration is made in the aspect that the composition of the present invention is used in the oral cavity, of these cationic bactericidal agents, from the viewpoint of a balance between the safety and the bactericidal effects, it is preferable to use a quaternary ammonium salt represented by the above-mentioned general formula (I):

[Ka 12]

(I)

wherein each of $R_1$, $R_2$, $R_3$, and $R_4$ is independently a substituted or unsubstituted, saturated or unsaturated, and branched or linear aliphatic group having 1 to 30 carbon atoms, for example, an alkyl group, an arylalkyl group, an alkoxyalkyl group, a polyoxyalkyl group, an alkylamide alkyl group, an alkylsulfamide alkyl group, a hydroxyalkyl group, a halogen atom-substituted alkyl group, or the like; or an aromatic group, for example, an aryl, an alkylaryl, or the like, or two or three of any of $R_1$, $R_2$, $R_3$, and $R_4$ may be connected to form a ring; and $X^-$ is an anion selected from a halide (for example, a chloride, a bromide, or an iodide), an acetate, a citrate, a lactate, a glycolate, a phosphate, a nitrate, a sulfate, an alkyl sulfate, an aryl sulfate, an alkylaryl sulfate, a perchlorate, and a tetrafluoroborate; and a quaternary ammonium salt represented by the above-mentioned general formula (IV):

[Ka 13]

(IV)

wherein $R_{11}$ is a substituted or unsubstituted, saturated or unsaturated, and branched or linear aliphatic group having 1 to 30 carbon atoms, for example, an alkyl group, an arylalkyl group, an alkoxyalkyl group, a polyoxyalkyl group, an alkylamide alkyl group, an alkylsulfamide alkyl group, a hydroxyalkyl group, a halogen atom-substituted alkyl group, or the like; or an aromatic group, for example, an aryl, an alkylaryl, or the like; and $X^-$ is an anion selected from a halide (for example, a chloride, a bromide, or an iodide), an acetate, a citrate, a lactate, a glycolate, a phosphate, a nitrate, a sulfate, an alkyl sulfate, an aryl sulfate, an alkylaryl sulfate, a perchlorate, and a tetrafluoroborate.

Among the compounds represented by the general formulas (I) and (IV) mentioned above, compounds having a critical micelle concentration of 10 mM or lower are preferably used, and compounds having a critical micelle concentration of 1 mM or lower are more preferably used, and those having a critical concentration of 0.001 to 0.5 mM are even more preferably used. Specifically, it is preferable that at least one of $R_1$, $R_2$, $R_3$, and $R_4$, or $R_{11}$ has 12 or more carbon atoms, and a chloride or a phosphate is preferred as a counter anion. The compound as described above includes octadecyltrimethylammonium chloride, tetradecyldimethylbenzylammonium chloride, octadecyldimethylbenzylammonium chloride, cetylpyridinium chloride, and the like, and octadecyldimethylbenzylammonium chloride and cetylpyridinium chloride are preferred.

Besides those listed above, cationic surfactants including commercially available products described in, for example, "13398 no Kagaku Shohin (The Chemical Daily Co., Ltd., Japan) (13398 Chemical Commercial Products (The Chemical Daily Co., Ltd., Japan))," pages 1203-1205, "Handbook of Industrial Surfactants, 2nd Edition, Vol. 2" (Gower), "Surfactant systems" (Chapman and hall), "Industrial surfactants" (NOYES), "Shin-ban Kaimen Kasseizai Handbook (New Edition Surfactant Handbook)" (Kougakutosho Ltd.), or the like can be used. Commercially available products are quaternary ammonium salts of fatty acids, benzalkonium salts, benzethonium chloride, pyridinium salts, imidazolinium salts, and the like, and the quaternary ammonium salts of fatty acids and the benzalkonium salts can be preferably used, and the benzalkonium salts can be more preferably used. Commercially available benzalkonium salts include CATION F2-35R, CATION F2-40E CATION F2-50, CATION F2-50E (hereinabove, manufactured by NOF CORPORATION), ARQUAD CB-50 (manufactured by Lion), CATIOGEN S, CATIOGEN TMS-C (hereinabove, manufactured by DAI-ICHI KOGYO SEIYAKU CO., LTD.), TEXNOL (manufactured by Nippon Nyukazai Co., Ltd.), and the like.

The use of the cationic bactericidal agent is not limited to a single kind, but a plural cationic bactericidal agents may be mixed in a given ratio. In addition, a commercially available cationic bactericidal agent, which is a mixture of plural compounds due to difference in alkyl groups and the like may be used.

The solvent (c) usable in the present invention refers to a liquid having a boiling point within the range of from 40° to 180° C. at an ambient pressure (101.3 kPa), and the solvent includes, for example, water; alcohols such as methanol, ethanol, isopropanol, n-propanol, butanol, and cyclohexanol; halogens such as chloroform, methylene chloride, and chlorobenzene; hydrocarbons such as hexane, cyclohexane, toluene, and xylene; ketones such as acetone, methyl ethyl ketone, and cyclohexanone; esters such as ethyl acetate and butyl acetate; ethers; and the like, and the present invention is not limited to those exemplified above. However, in consideration of the fact that the composition of the present invention is mainly used in the oral cavity in most cases, among these solvents, water and ethanol are preferred. In addition, water and ethanol may be properly mixed in a given ratio and used.

The phosphorylated saccharide (a) is contained in an amount of preferably from 0.001 to 10% by weight, more preferably from 0.005 to 2% by weight, and even more preferably from 0.01 to 1% by weight, of the composition, from the viewpoint of detaining the cationic bactericidal agent on the surfaces of the teeth more effectively.

The cationic bactericidal agent (b) is contained in an amount of preferably from 0.0001 to 5% by weight, more preferably from 0.0005 to 2% by weight, and even more preferably from 0.001 to 1% by weight, of the composition, from the viewpoint of balance between safety and bactericidal effect and lastingness of the bactericidal effect.

The solvent (c) is contained in an amount of preferably from 50 to 99.998% by weight, more preferably from 70 to 99.998% by weight, and even more preferably from 90 to 99.998% by weight, of the composition, from the viewpoint of providing the composition with an excellent operability and homogeneously dissolving the bactericidal agent and the phosphorylated saccharide.

In addition, it is desired that the formulation ratio of the phosphorylated saccharide (a) to the cationic bactericidal agent (b), i.e. (a)/(b), is preferably within the range of from 0.05 to 200 (weight ratio), more preferably from 0.1 to 100, even more preferably from 0.1 to 50, even more preferably from 0.2 to 50, even more preferably from 0.2 to 10, even more preferably from 0.2 to 5, even more preferably within the range of from 0.5 to 2. In addition, if the total sum of (a) and (b) is 1 part by weight, the solvent (c) is formulated in an amount of preferably within the range of from 1 to 49,999 parts by weight, and more preferably within the range of from 100 to 10,000 parts by weight.

Since the composition of the present invention is assumed to be used in the oral cavity, it is desired that the composition has a pH near neutrality. In addition, it is desired that the composition of the present invention has a pH range adjusted to preferably from 4 to 9, more preferably from 5 to 8, and even more preferably from 6 to 7.5, from the viewpoint of maximally exhibiting the effect of the bactericidal agent contained in the composition of the present invention. The pH of the composition of the present invention can be adjusted depending upon the kinds of the phosphorylated saccharide (a) and the cationic bactericidal agent (b) used, and their respective formulation ratio and concentrations. Also, a pH adjusting agent may be further added thereto. As the pH adjusting agent, a known one can be used without any limitations, and the agent includes, for example, organic acids such as acetic acid, citric acid, DL-malic acid, succinic acid, and fatty acids and salts thereof; carbonates such as sodium carbonate and calcium carbonate; phosphoric acids such as phosphoric acid and salts thereof; various amino acids such as glycine, alanine, aspartic acid, and glutamic acid and salts thereof; and amines such as triethanolamine.

Further, the dental composition for oral use of the present invention can be formulated with a flavor, a nonionic surfactant, an anionic surfactant, a viscosity-adjusting agent, a polyhydric alcohol, a buffering agent, other pharmaceutically effective agent, a sweetener, a colorant, an antioxidant, an abrasive, or the like, as occasion demands.

As an example of the flavor, an oil-soluble flavor is preferably used. The flavor including, for example, not only a synthetic flavor such as menthol, carvone, anethole, eugenol, cineol, thymol, methyl salicylate, pulegone, menthone, pinene, limonene, or menthyl acetate, but also a natural purified oil, such as a mint oil, such as peppermint oil, spearmint oil, or Japanese mint oil, a citrus oil, such as lemon, orange, grapefruit, or lime, and a herb oil, such as eucalyptus, sage, rosemary, thyme, laurel, basil, labiate, bay, estragon, parsley, celery, or coriander, a spice oil, such as cinnamon, pepper, nutmeg, mace, clove, ginger, cardamon, or anise; or a fruit flavor, such as apple, banana, melon, grape, peach, strawberry, blueberry, raspberry, black currant, litchi, star fruit, passion fruit, plum, pineapple, or muscat, or the like can be used. Among these oil-soluble flavors, menthol, carvone, peppermint oil, spearmint oil, Japanese mint oil, methyl salicylate, cineol, limonene, and pinene are more preferred, from the viewpoint of giving a refreshing taste and savoriness to the oral cavity. These oil-soluble flavors are used singly or in a combination of two or more kinds. It is desired that these oil-soluble flavors are contained in an amount of preferably from 0.1 to 1% by weight, more preferably from 0.2 to 0.6% by weight, and even more preferably from 0.3 to 0.5% by weight, of the dental composition for oral use of the present invention, from the viewpoint of obtaining a masking effect to a foreign taste of a cationic bactericidal agent.

The nonionic surfactant includes, sugar fatty acid esters, polyglycerol fatty acid esters, polyoxyethylene hydrogenated castor oil, sorbitan fatty acid esters, polyoxyethylene polyoxypropylene block copolymer-type nonionic surfactants, fatty acid alkanolamides, polyoxyethylene fatty acid esters, fatty acid monoglycerides, polyoxyethylene alkyl ethers, and the like. Among them, it is preferable that the nonionic surfactant includes a polyglycerol fatty acid ester, a sucrose fatty acid ester, a maltose fatty acid ester, or a lactose fatty acid ester, from the viewpoint of suppressing the formation of dental plaques. It is desired that these nonionic surfactants are contained in an amount of preferably from 0.01 to 2% by weight, more preferably from 0.05 to 1% by weight, and even more preferably from 0.1 to 0.8% by weight, of the dental composition for oral use of the present invention.

The anionic surfactant includes alkyl sulfuric esters, such as sodium lauryl sulfate and sodium myristyl sulfate; N-acylamino acid salts, such as lauroylsarcosine sodium; acyl taurine salts, such as lauroyl methyltaurine sodium; sulfonates of fatty acids, such as sodium ethyl coconut oil fatty acid sulfonic esters; and the like.

It is preferable that these anionic surfactants are contained in an amount of 0.01% by weight or less, i.e. 0 to 0.01% by weight, of the dental composition for oral use, from the viewpoint of irritation, adsorption of the cationic bactericidal agent to the teeth, and the like.

The viscosity-adjusting agent includes cellulose derivatives such as carboxymethyl cellulose sodium and hydroxyethyl cellulose; alginic acid derivatives, such as sodium alginate and propylene glycol alginate; gums such as carrageenan, xanthane gum, gellan gum, tragacanth gum, and karaya gum; synthetic binding agents such as polyvinyl alcohol, sodium polyacrylate and vinyl carboxylate polymers; inorganic binding agents, such as AEROSIL (highly dispersible silica), VEEGUM, and LAPONITE; starch degradation products, such as dextrin and reducing dextrin; and the like. These viscosity controlling agents can be used singly or in a mixture of two or more kinds.

The polyhydric alcohol includes propylene glycol, glycerol, polyethylene glycol, and the like. The buffering agent includes citric acid and salts thereof, malic acid and salts thereof, phosphoric acid and salts thereof, and the like. The sweetener includes saccharin sodium, acesulfame potassium, stevioside, neohesperidyl dihydrochalcone, glycyrrhizin, perillartine, thaumatin, asparatyl phenylalanyl methyl ester, sucrose, and the like.

Other pharmaceutically effective agent includes one or more compounds selected from antiplasmin agents such as tranexamic acid and epsilon($\epsilon$)-aminocaproic acid; vitamins such as ascorbic acid and tocopherol ester; glycyrrylitinates; allantoins; plant extracts from *Phellodendron amurense*, *Scutellaria baicalensis* root, *Matricaria chamomilla* flower, *Krameria triandra* root, and *Commiphora myrrha*, or the like; enzymes such as dextranase, mutanase, and lysozyme chloride; salts such as sodium chloride, potassium nitrate, carbonates, bicarbonates, and sesquicarbonates; sodium copper chlorophyllin, copper gluconate, zinc chloride, zeolite, water-soluble inorganic phosphoric acid compounds, aluminum lactate, and the like.

The colorant includes legal dyes such as Red No. 1, Red No. 3, Red No. 105, Yellow No. 4, Yellow No. 203, Blue No. 1, Blue No. 2, Green No. 3, and Green No. 201, and pigments such as titanium oxide and ultramarine.

In addition, a water-soluble metal fluoride such as sodium fluoride, sodium monofluorophosphate, or stannous fluoride may be favorable formulated. If a metal fluoride as mentioned above is formulated, fluorine ions are incorporated into the teeth upon contacting the composition of the present invention with surfaces of the teeth, so that fluoroapatite is formed on the surfaces of the teeth, whereby an effect of enhancing anti-caries formation of the teeth can be expected.

The composition of the present invention is not particularly limited, so long as the composition contains a phosphorylated saccharide (a), a cationic bactericidal agent (b), and a solvent (c) in a given content, and the composition can be easily produced by a known method by one of ordinary skill in the art.

EXAMPLES

The present invention will be specifically described hereinbelow by the Examples, without intending to limit the scope of the present invention thereto.

Production Example 1

Synthesis of Phosphorylated Pullulan

In a flask having an inner volume of 500 mL, 8.5 g of pullulan (purchased from HAYASHIBARA SHOJI, INC.) was dissolved in 38.5 mL of distilled water at room temperature. While stirring this solution, 189 g of a 1 M aqueous phosphoric acid solution, of which pH was adjusted with sodium hydroxide to 5.5, was added over 10 minutes. After the addition, the stirring was continued for an additional 1 hour. Thereafter, the distilled water was distilled off in a volume of about 200 mL at a temperature between 100° and 103° C., the stirring was then continued at 170° C. for 5 hours, and the reaction product was cooled to room temperature. The reaction product was taken out and pulverized with a mortar and pestle, go give 23.43 g of a brown solid.

The amount 23.43 g of the brown solid obtained above was dissolved in 680 mL of distilled water. While stirring this solution, 1100 mL of 99.5% ethanol was added to the solution over 10 minutes. Concurrently with the addition, the formation of the precipitates was confirmed. After the termination of the addition, the mixture was continued stirring for an additional 1 hour. The mixture was then allowed to stand to separate into layers, and the supernatant was removed by decantation, and the residual precipitates were washed twice with 250 mL of a 50% by volume aqueous ethanol solution. The precipitates were dissolved in distilled water (30 mL), and the solution was added to ethanol (700 mL) in an agitated state gradually each in a small amount, over 5 minutes. The sedimented precipitates were collected by filtration with a glass filter (3G), washed with 99.5% ethanol (50 mL), and dried at 60° C. under a reduced pressure (1.5 kPa) for 3 hours, to give 8.5 g of a slightly brownish white solid.

The white solid obtained was subjected to an IR spectroscopy (KBr tablet method). As a result, peaks ascribed to the phosphate site were observed at 1000 to 1200 $cm^{-1}$. In addition, the white solid was subjected to an elemental analysis of phosphorus atom according to ICP emission spectroscopy. As a result, it was found that the phosphorus was contained in an amount of 2.52% by weight. From the results, it was judged that about 4.7% by number of the hydroxyl groups of the pullulan had undergone phosphorylation. In addition, the white solid was further subjected to GPC analysis (column: TSK gel α-M, mobile phase: 0.1 M-aqueous NaCl solution). As a result, the white solid had a number-average molecular weight (Mn) of 18,500. Here, the ICP emission spectroscopy was carried out by weighing 40 mg of the above-mentioned white solid, and subjected to oxygen flask combustion using 20 mL of 5 N nitric acid as an absorbed liquid, and the absorbed liquid was used as a test solution. The analytical apparatus and the measurement conditions are follows.

ICP Emission Spectrophotometer: Model IRIS-AP, manufactured by Jarrell-Ash
High-frequency output: 1150 W
Flow rate (Ar) for supplementary gas: 0.5 L/min.
Flow rate (Ar) for nebulizer: 180 kPa
Rotational speed of the pump: 130 r/min

From the values for elemental analysis of phosphorus thus obtained, the ratio of the hydroxyl groups that are subjected to phosphorylation of the hydroxyl groups of the pullulan was calculated by the following method.

The structural formula for the pullulan is a repeating unit having the following structure. Thus, the molecular formula for the pullulan is represented by the molecular formula $(C_{36}H_{60}O_{30})_n$, i.e. $\{C_{36}H_{42}O_{12}(OH)_{18}\}_n$. Of the hydroxyl groups in the structure, supposing that x number of hydroxyl groups are phosphorylated, the molecular formula is represented by the molecular formula $[C_{36}H_{42}O_{12}(OH)_{18-x}\{OPO(OH)_2\}_x]_n$. Since the value for elemental analysis of phosphorus in this molecular formula is 2.52%, the following relational formula can be derived.

30.97×x/{12.01×36+1.008×42+16.00×12+17.01×(18−x)+96.99×x}×100=2.52

If the formula is solved for x, x is 0.35. Thus, it was found that of the hydroxyl groups of the pullulan, 0.85/18×100=4.7 number (%) of hydroxyl groups were subjected to phosphorylation.

Formula $(C_{36}H_{60}O_{30})n$
$C_{36}H_{60}O_{30} = C_{36}H_{42}O_{12}(OH)_{18}$

[Ka 14]

Example 1

A solution prepared by dissolving 0.1 g of cetyl pyridinium chloride (hereinafter referred to as "CPC") as a cationic bactericidal agent and 0.1 g of the phosphorylated pullulan synthesized in Production Example 1 mentioned above as a phosphorylated saccharide in 10 g of water was diluted 100-folds with water, to prepare a composition containing CPC and phosphorylated pullulan each in an amount of 0.01% by weight, and water in an amount of 99.98% by weight, to provide a composition of Example 1 of the present invention. Here, this composition had a pH of 7.0.

Example 2

The amount 0.1 g of CPC as a bactericidal agent and 0.1 g of phosphorylated pullulan synthesized in Production Example 1 as a phosphorylated saccharide were dissolved in 10 g of water, to prepare a composition containing CPC and phosphorylated pullulan each in an amount of 1% by weight and 98% by weight of water, to provide a composition of Example 2 of the present invention. Here, this composition had a pH of 6.6.

Example 3

A solution prepared by dissolving 0.1 g of CPC as a bactericidal agent and 0.2 g of the phosphorylated pullulan synthesized in Production Example 1 as a phosphorylated saccharide in 10 g of water was diluted 100-folds with water, to prepare a composition containing CPC in an amount of 0.01% by weight, phosphorylated pullulan in an amount of 0.02% by weight, and water in an amount of 99.97% by weight, to provide a composition of Example 3 of the present invention. Here, this composition had a pH of 6.9.

Comparative Example 1

A composition containing only water, without containing CPC and phosphorylated pullulan was prepared, to provide a composition of Comparative Example 1 (control). Here, this composition had a pH of 6.9.

Comparative Example 2

The amount 0.1 g of CPC was dissolved in 10 g of water, to prepare a composition containing CPC in an amount of 1% by weight and water in an amount of 99% by weight, to provide a composition of Comparative Example 2. Here, this composition had a pH of 6.0.

Comparative Example 3

The amount 0.1 g of phosphorylated pullulan was dissolved in 10 g of water, to prepare a composition containing phosphorylated pullulan in an amount of 1% by weight and water in an amount of 99% by weight, to provide a composition of Comparative Example 3. Here, this composition had a pH of 6.9.

Comparative Example 4

A solution prepared by dissolving 0.1 g of CPC in 10 g of water was diluted 100-folds with water, to prepare a composition containing CPC in an amount of 0.01% by weight and water in an amount of 99.99% by weight, to provide a composition of Comparative Example 4. Here, this composition had a pH of 6.7.

The physical properties of Examples 1 to 3 and Comparative Examples 1 to 4 obtained were evaluated in accordance with the methods of the following Test Examples 1 and 2. Here, regarding Test Example 2, the evaluation was made on only on the compositions of Example 1 and Comparative Example 4.

Test Example 1

Adhesion Test of Bacteria to Surfaces of Teeth

As a test method for evaluating an effect of suppressing bacterial adhesion to surfaces of the teeth of each of the compositions of Examples 1 to 3 and Comparative Examples 1 to 4, the evaluation was made by previously applying the composition to a synthetic apatite surface, and observing the amount of adhesion of S. mutans on this surface with an electron microscope. Concrete procedures are as follows. The evaluation results for Examples 1 to 3 and Comparative Examples 1 to 4 are shown in FIGS. 1 to 7, respectively.

(1) Culture of S. mutans

As a bacterium in the oral cavity, Streptococcus mutans 854S (S. mutans), a bacterium causative of dental caries, was used. S. mutans is cultured using a medium (TSBY) in which 0.5% yeast extract (Bacto™ Yeast Extract; manufactured by Becton, Dickinson and Company) is added to a tryptic soy broth (Bacto™ Tryptic Soy Broth: Soybean-Casein Digest Medium; manufactured by Becton, Dickinson and Company) at 37° C. under aerobic conditions. Here, upon the formation of a biofilm on S. mutans, one prepared by adding 5% by weight sucrose to the TSBY is used as a medium. S. mutans is cultured to a logarithmic growth phase. Thereafter, the absorbance was determined (SPECTRONIC 20A, manufactured by SPECTRONIC) at a wavelength of 570 nm, and a suspension of S. mutans was prepared using a medium in which 5% by weight sucrose is added to the TSBY so as to have a concentration of $1 \times 10^5$ cfu/mL.

(2) Treatment to Apatite Surfaces

Four milliliters of each of the compositions of Examples 1 to 3 or Comparative Examples 1 to 4 is taken into a cylindrical vessel having a diameter of 22 mm and a depth of 17.5 mm, and an apatite test plate (10 mm×10 mm×2 mm, manufactured by PENTAX Corporation, apatite pellet APP-101, the surface being mirror-polished) is immersed into the cylindrical vessel. The apatite test plate is immersed at 37° C. for 12 hours, and an apatite test plate is then taken out into a fresh cylindrical vessel, and immersed in distill water and washed twice, and the washed test plate is air-dried.

(3) Proliferation of S. mutans on Apatite Surface

Four milliliter of the suspension of S. mutans prepared in accordance with the method of the above (1) is poured into a cylindrical vessel having a diameter of 22 mm and a depth of 17.5 mm, and an apatite test plate treated with each of the compositions of Examples 1 to 3 or Comparative Examples 1 to 4 is immersed therein according to the method of the above (2). The cells are cultured at 37° C. for 12 hours under aerobic conditions, the apatite test plate is then taken out, and S. mutans adhered to this surface is observed with a scanning electron microscope (SEM) in accordance with the following procedures to observe the state of proliferation.

(4) Electron Microscope Observation of S. mutans on Apatite Surface

Sodium cacodylate in an amount of 0.01 mol and sodium chloride in an amount of 0.15 mol are dissolved in 1 liter of distilled water, to prepare a cacodylate buffer (pH 7.0±0.2). The apatite test plate after being cultured as described in the above (3) is immersed in the cacodylate buffer previously warmed to 37° C., and allowed to stand therein for 10 minutes. The procedures are carried out twice, and the apatite test plate is washed.

The test plate after being washed is immersed in an immobilization solution (solution containing 1% glutaraldehyde, 0.01 M sodium cacodylate, and 0.15 M NaCl), and allowed to stand for 10 minutes. Thereafter, the test plate is taken out from the immobilization solution, and immersed again in a fresh similar immobilization solution, and allowed to stand for 30 minutes to immobilize S. mutans.

The test plate is transferred to a fresh cacodylate buffer and immersed for 15 minutes, the washing procedures being repeated twice. Subsequently, the test plate is immersed sequentially in 50% ethanol, 70% ethanol, 90% ethanol, and 95% ethanol (volume ratio) for 15 minutes each, and finally an immersion procedure in 100% ethanol is repeated twice, and dehydrated (15 minutes each).

Next, this test plate is immersed in isoamyl acetate to replace ethanol with isoamyl acetate. The immersion procedure in isoamyl acetate is repeated twice, and the immersion time for the first immersion is 30 minutes, and that for the second immersion is 12 hours. Thereafter, the test plate is dried with a critical point dryer, the test plate obtained is subjected to Pt—Pd coating with an ion coater, to prepare a test plate for the SEM observation, and the test plate observed with an SEM.

Test Example 2

Adsorption Test of Composition on Surfaces of Teeth

As a model test for evaluating the adsorption of a composition to surfaces of the teeth, the evaluation is made using a crystal oscillator microbalance (hereinafter referred to as QCM) measuring apparatus (Model D300, manufactured by Q-Sense, Q-Sense Crystal QSX-327 being used as an apatite plate). This evaluation method utilizes the matter that if a component such as a bactericidal agent is adsorbed to surfaces of apatite oscillated at a constant frequency, the oscillating frequency changes. In other words, the larger the change in frequency, the more the amount of the adsorbed component.

Figure 1:
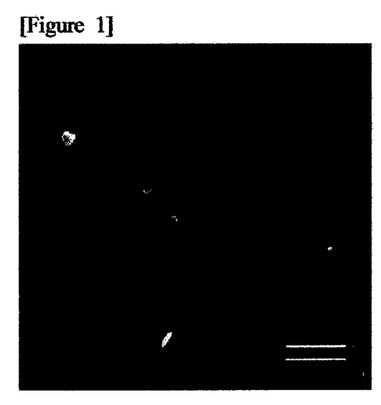
FIG. 1 is an electron micrograph of an adhesion test of bacteria to surfaces of apatite of Example 1. Here, the scale bar in the figure indicates 20 μm.
Figure 2:
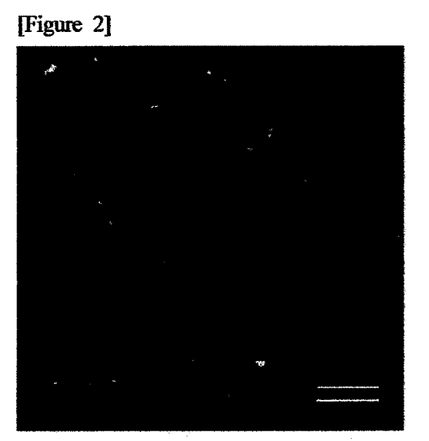
FIG. 2 is an electron micrograph of an adhesion test of bacteria to surfaces of apatite of Example 2. Here, the scale bar in the figure indicates 20 μm.
Figure 3:
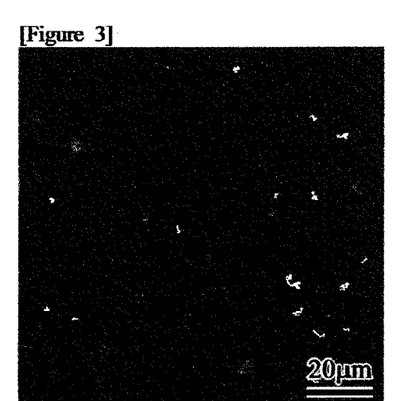
FIG. 3 is an electron micrograph of an adhesion test of bacteria to surfaces of apatite of Example 3. Here, the scale bar in the figure indicates 20 μm.
Figure 4:
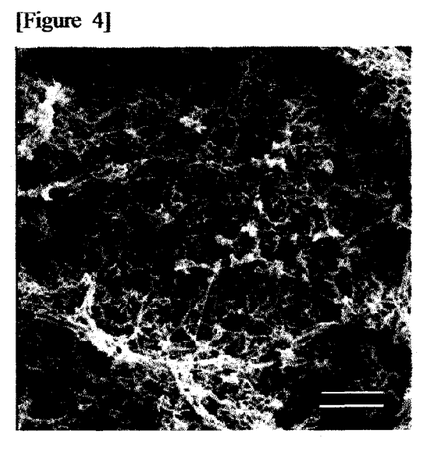
FIG. 4 is an electron micrograph of an adhesion test of bacteria to surfaces of apatite of Comparative Example 1. Here, the scale bar in the figure indicates 20 μm.
Figure 5:
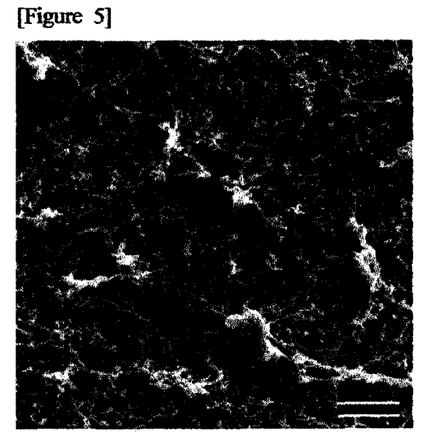
FIG. 5 is an electron micrograph of an adhesion test of bacteria to surfaces of apatite of Comparative Example 2. Here, the scale bar in the figure indicates 20 μm.
Figure 6:
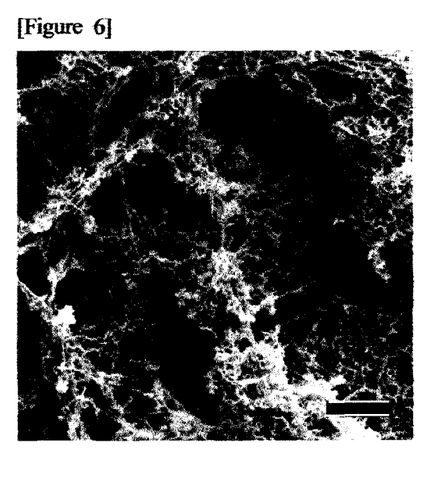
FIG. 6 is an electron micrograph of an adhesion test of bacteria to surfaces of apatite of Comparative Example 3. Here, the scale bar in the figure indicates 20 μm.
Figure 7:
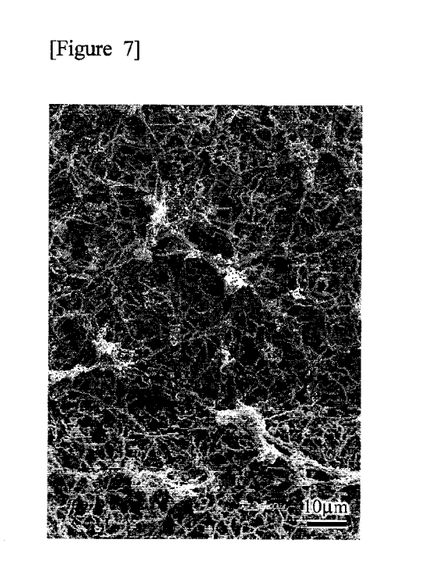
FIG. 7 is an electron micrograph of an adhesion test of bacteria to surfaces of apatite of Comparative Example 4. Here, the scale bar in the figure indicates 10 μm.
Figure 8:
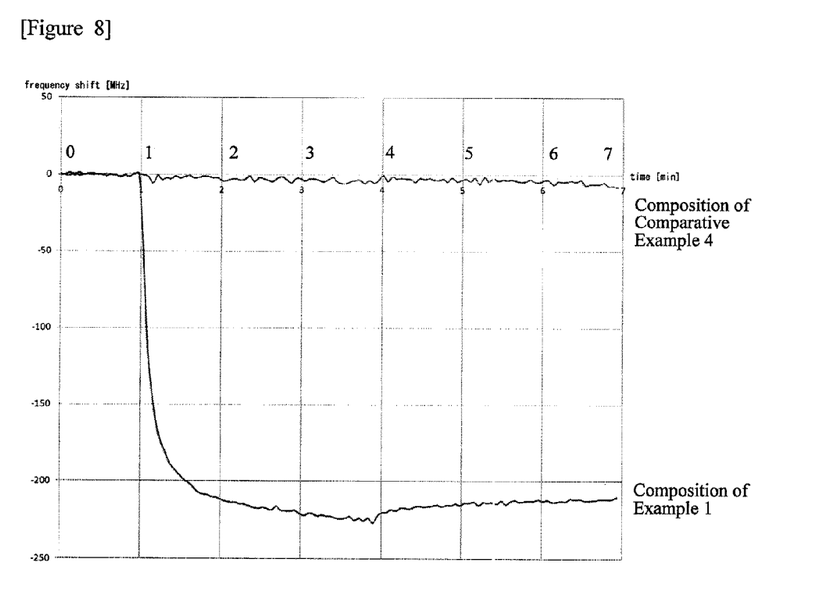
FIG. 8 is a chart showing evaluation results for adsorption to surfaces of apatite of Example 1 and Comparative Example 4.

Concrete procedures are as follows. As to the condition of adsorption of the compositions of Example 1 and Comparative Example 4 to the surfaces of the teeth, the results are shown in FIG. 8 (the axis of abscissa is the time course, and the axis of ordinates is change in frequency).

The apatite plate is set in a measurement chamber of the QCM measuring apparatus, distilled water is introduced into the chamber while oscillating the chamber at 25 MHz, and the apatite plate is immersed in distilled water (temperature 23.5° C.). This state is maintained for 4 minutes, and whether the number of oscillations is subjected to transition is at a given level is confirmed. The composition of Example 1 or Comparative Example 4 is then introduced into the chamber, a sensor is set within the chamber, and an oscillating frequency is measured. After 3 minutes passed from the introduction of the composition, the solution inside the chamber is replaced with distilled water, and an oscillating frequency is further measured.

It could be seen from the results of Test Example 1 that the bacteria are hardly adhered to the apatite surfaces that are surface-treated with the compositions of Examples 1 to 3 in which a bactericidal agent (CPC) and phosphorylated pullulan are used together. It could be seen from the results of Test Example 2 that the frequency is found to rapidly drop in the composition of Example 1, the measuring frequency being lowered by 211 Hz after 1 minute, lowered by 220 Hz after 2 minutes, and lowered by 224 Hz after 3 minutes, showing nearly an equilibrium state on 2 minutes or later. In other words, it is suggested that in a 1-minute immersion treatment, up to 94% of the composition of that of the equilibrium state (the state after 3 minutes) is adsorbed. In addition, it is shown from the matter that the frequency remain being lowered even 3 minutes or later, so that once phosphorylated pullulan and CPC are adsorbed, these components are hardly removed. Upon considering the above results collectively, by using phosphorylated pullulan and the bactericidal agent together, it is considered that if the bactericidal agent is once adsorbed to and held by phosphorylated pullulan, the bactericidal agent is held to the apatite surface even after washing, thereby making it possible to effectively suppress the propagation of the bacteria. Especially, as is clear from the test results using the composition of Example 1, it could be seen that the bactericidal agent is quickly adsorbed, that the desired effects are exhibited even at a very low concentration of 0.01% by weight, and that the effects are lasting even in a long time period of 12 hours.

On the other hand, the bacterial adhesion on the apatite surfaces that are surface-treated with a comparative composition which lacks either a bactericidal agent or phosphorylated pullulan (Comparative Examples 2 to 4) is hardly different that of the apatite surface that is surface-treated with a control composition (Comparative Example 1), and a large number of bacteria are adhered (Test Example 1). It is suggested from the results of Test Example 2 that in the composition of Comparative Example 4, only a slight lowering of frequency of 4.0 Hz is found upon immersion with the CPC solution; therefore, as compared to the results of the frequency being lowered by as much as 224 Hz found in the composition of Example 1, the amount of the CPC adsorbed to the apatite surface is slight in the solution containing only the CPC. From the above, most of the applied bactericidal agent is undesirably run off without being hardly held to the apatite surface in Comparative Example 2 or 4 in the Test Example 1, so that it is considered that the bacteria are adhered in the same level as the apatite surface that is surface-treated with the control composition. In addition, only phosphorylated pullulan is present on the apatite surface in Comparative Example 3 of Test Example 1, so that bacterial adhesion could not be suppressed. It is confirmed from the results that the phosphorylated pullulan alone does not have any effects of suppressing bacterial adhesion.

It could be seen from the above results that phosphorylated pullulan plays a key role in holding the bactericidal agent, so that the bacterial adhesion can be suppressed over a long period of time by using the phosphorylated pullulan and the bactericidal agent together.

The dental composition for oral use of the present invention can be suitably used for, for example, a mouse-wash agent, a dentifrice agent, a gargling agent, a mouse spray, a coating agent or a bonding agent to tooth surface or a dental prosthetic, a hypersensitive inhibitor, a therapeutic agent for periodontal diseases, that is applied to a periodontal pocket, or the like.

The invention claimed is:

1. A dental composition for oral use, comprising:
   a phosphorylated pullulan (a) having a number-average molecular weight Mn of 10,000 to 100,000,
   a cationic bactericidal agent (b) and
   a solvent (c),
   wherein the phosphorylated pullulan (a) and the cationic bactericidal agent (b) are formulated in a weight ratio (a)/(b) of from 0.2 to 5,
   wherein hydroxyl groups of the phosphorylated pullulan (a) are phosphorylated in an amount of 2 to 10% by number and
   wherein the cationic bactericidal agent (b) is at least one cationic bactericidal agent selected from the group consisting of:

a quaternary ammonium salt represented by the general formula (I):

wherein each of $R_1$, $R_2$, $R_3$, and $R_4$ is independently a substituted or unsubstituted, saturated or unsaturated, branched or linear aliphatic group having 1 to 30 carbon atoms or an aromatic group and wherein two or three of any of $R_1$, $R_2$, $R_3$, and $R_4$ are optionally connected to form a ring; and X– is an anion selected from a halide, an acetate, a citrate, a lactate, a glycolate, a phosphate, a nitrate, a sulfate, an alkyl sulfate, an aryl sulfate, an alkylaryl sulfate, a perchlorate, and a tetrafluoroborate;

a quaternary ammonium salt represented by the general formula (II):

wherein each of $R_5$, $R_6$, $R_7$, $R_8$, $R_9$, and $R_{10}$ is independently a substituted or unsubstituted, saturated or unsaturated, branched or linear aliphatic group having 1 to 30 carbon atoms or an aromatic group and wherein two or three of any of $R_5$, $R_6$, $R_7$, $R_8$, $R_9$, and $R_{10}$ are optionally connected to form a ring;

$L_1$ is a substituted or unsubstituted divalent linking group, and

X– is an anion selected from a halide, an acetate, a citrate, a lactate, a glycolate, a phosphate, a nitrate, a sulfate, an alkyl sulfate, an aryl sulfate, an alkylaryl sulfate, a perchlorate, and a tetrafluoroborate;

a quaternary ammonium salt represented by the general formula (IV):

wherein $L_1$ is a substituted or unsubstituted, saturated or unsaturated, branched or linear aliphatic group having 1 to 30 carbon atoms or an aromatic group; and X– is an anion selected from a halide, an acetate, a citrate, a lactate, a glycolate, a phosphate, a nitrate, a sulfate, an alkyl sulfate, an aryl sulfate, an alkylaryl sulfate, a perchlorate, and a tetrafluoroborate;

a pyridinium salt represented by the general formula (V):

wherein L$_2$ is a substituted or unsubstituted divalent linking group; and

X− is an anion selected from a halide, an acetate, a citrate, a lactate, a glycolate, a phosphate, a nitrate, a sulfate, an alkyl sulfate, an aryl sulfate, an alkylaryl sulfate, a perchlorate, and a tetrafluoroborate; and a quaternary ammonium salt represented by the general formula (VII):

(VII)

wherein each of R$_{12}$ and R$_{13}$ is independently a substituted or unsubstituted, saturated or unsaturated, branched or linear aliphatic group having 1 to 30 carbon atoms or an aromatic group; and X− is an anion selected from a halide, an acetate, a citrate, a lactate, a glycolate, a phosphate, a nitrate, a sulfate, an alkyl sulfate, an aryl sulfate, an alkylaryl sulfate, a perchlorate, and a tetrafluoroborate.

2. The dental composition for oral use according to claim 1, wherein the phosphorylated pullulan is contained in an amount of from 0.001 to 10% by weight.

3. The dental composition for oral use according to claim 1, wherein:

in general formula (I) the substituted or unsubstituted, saturated or unsaturated, branched or linear aliphatic group having 1 to 30 carbon atoms is selected from the group consisting of an alkyl group, an arylalkyl group, an alkoxyalkyl group, a polyoxyalkyl group, an alkylamide alkyl group, an alkylsulfamide alkyl group, a hydroxyalkyl group, and a halogen atom-substituted alkyl group, the aromatic group is selected from the group consisting of an aryl and alkylaryl group; and the halide is selected from the group consisting of chloride, bromide, and iodide;

in general formula (II) the substituted or unsubstituted, saturated or unsaturated, branched or linear aliphatic group having 1 to 30 carbon atoms is selected from the group consisting of an alkyl group, an arylalkyl group, an alkoxyalkyl group, a polyoxyalkyl group, an alkylamide alkyl group, an alkylsulfamide alkyl group, a hydroxyalkyl group, and a halogen atom-substituted alkyl group, the aromatic group is selected from the group consisting of an aryl and an alkylaryl group;

L$_1$ is a substituted or unsubstituted divalent linking group selected from the group consisting of an alkylene group, an arylene group, and an arylalkylene group; and the halide is selected from the group consisting of chloride, bromide, and iodide;

in general formula (IV) the substituted or unsubstituted, saturated or unsaturated, branched or linear aliphatic group having 1 to 30 carbon atoms is selected from the group consisting of an alkyl group, an arylalkyl group, an alkoxyalkyl group, a polyoxyalkyl group, an alkylamide alkyl group, an alkylsulfamide alkyl group, a hydroxyalkyl group, and a halogen atom-substituted alkyl group, and the aromatic group is selected from the group consisting of an aryl and an alkylaryl group; and the halide is selected from the group consisting of chloride, bromide, and iodide;

in general formula (V) L$_2$ is a substituted or unsubstituted divalent linking group selected from the group consisting of an alkylene group, an arylene group, and an arylalkylene group; and X− is an anion selected from the group consisting of a chloride, a bromide, an iodide, an acetate, a citrate, a lactate, a glycolate, a phosphate, a nitrate, a sulfate, an alkyl sulfate, an aryl sulfate, an alkylaryl sulfate, a perchlorate, and a tetrafluoroborate; and in general formula (VII) the substituted or unsubstituted, saturated or unsaturated, branched or linear aliphatic group having 1 to 30 carbon atoms is selected from the group consisting of an alkyl group, an arylalkyl group, an alkoxyalkyl group, a polyoxyalkyl group, an alkylamide alkyl group, an alkylsulfamide alkyl group, a hydroxyalkyl group, and a halogen atom-substituted alkyl group, and the aromatic group is selected from the group consisting of an aryl and an alkylaryl group; and X− is an anion selected from the group consisting of a chloride, a bromide, an iodide, an acetate, a citrate, a lactate, a glycolate, a phosphate, a nitrate, a sulfate, an alkyl sulfate, an aryl sulfate, an alkylaryl sulfate, a perchlorate, and a tetrafluoroborate.

4. The dental composition for oral use according to claim 1, comprising a quaternary ammonium salt represented by the general formula (I).

5. The dental composition for oral use according to claim 1, comprising a quaternary ammonium salt represented by the general formula (II).

6. The dental composition for oral use according to claim 1, comprising a quaternary ammonium salt represented by the general formula (IV).

7. The dental composition for oral use according to claim 1, comprising a pyridinium salt represented by the general formula (V).

8. The dental composition for oral use according to claim 1, comprising a quaternary ammonium salt represented by the general formula (VII).

\* \* \* \* \*